Figure 3:
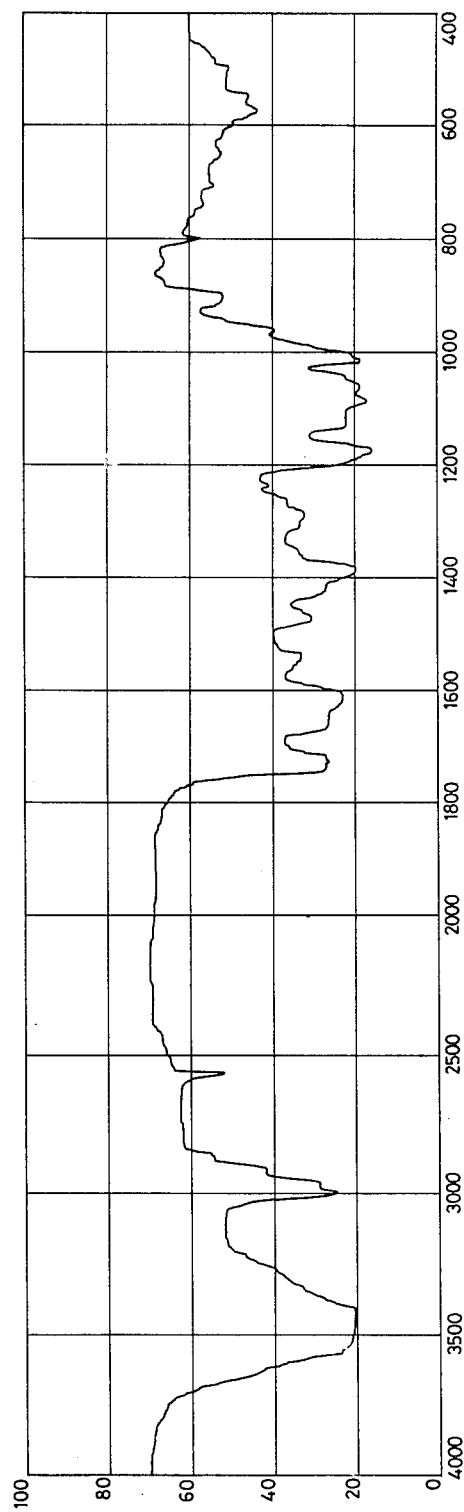

# United States Patent [19]

Gonella

[11] Patent Number: 4,476,120
[45] Date of Patent: Oct. 9, 1984

[54] THIOLIC DERIVATIVES OF ERYTHROMYCIN HAVING THERAPEUTIC ACTIVITY, AND PHARMACEUTICAL COMPOSITIONS CONTAINING THEM

[75] Inventor: Jacques Gonella, Zollikon Zurigo, Switzerland

[73] Assignee: Sigma Tau Indistrie Farmaceutiche Riunites, p.A, Rome, Italy

[21] Appl. No.: 344,960

[22] Filed: Feb. 2, 1982

[30]     Foreign Application Priority Data

Feb. 2, 1982 [FR]   France ........................................ 82 00821

[51] Int. Cl.$^3$ ...................... A61K 31/71; C07H 17/08
[52] U.S. Cl. .................................... 424/180; 536/7.2; 536/7.3; 536/7.4
[58] Field of Search ...................... 536/9, 7.2, 7.3, 7.4; 424/180

[56]              References Cited

U.S. PATENT DOCUMENTS

| | | | |
|---|---|---|---|
| 2,653,899 | 9/1953 | Bunch et al. ............................ | 536/9 |
| 2,743,268 | 4/1956 | Stieff ....................................... | 536/9 |
| 2,830,982 | 4/1958 | Stainbrook et al. .................... | 536/9 |
| 3,558,594 | 1/1971 | Jones et al. ............................. | 536/9 |
| 4,261,982 | 4/1981 | Luedders et al. ....................... | 536/9 |
| 4,264,765 | 4/1981 | Bodor et al. ............................ | 536/9 |

OTHER PUBLICATIONS

Kikuchi et al., "Chem. Abst.", vol. 93, 1980, p. 38279f.

*Primary Examiner*—Johnnie R. Brown
*Attorney, Agent, or Firm*—Cushman, Darby & Cushman

[57]              ABSTRACT

The thiolic salts of erythromycin and of the propionic ester of erythromycin with thenoyl alpha-mercaptopropionylglycine find therapeutical use in the cases in which erythromycin or its propionic ester are used and are generally endowed with very low toxicity and high hematic levels.

12 Claims, 5 Drawing Figures

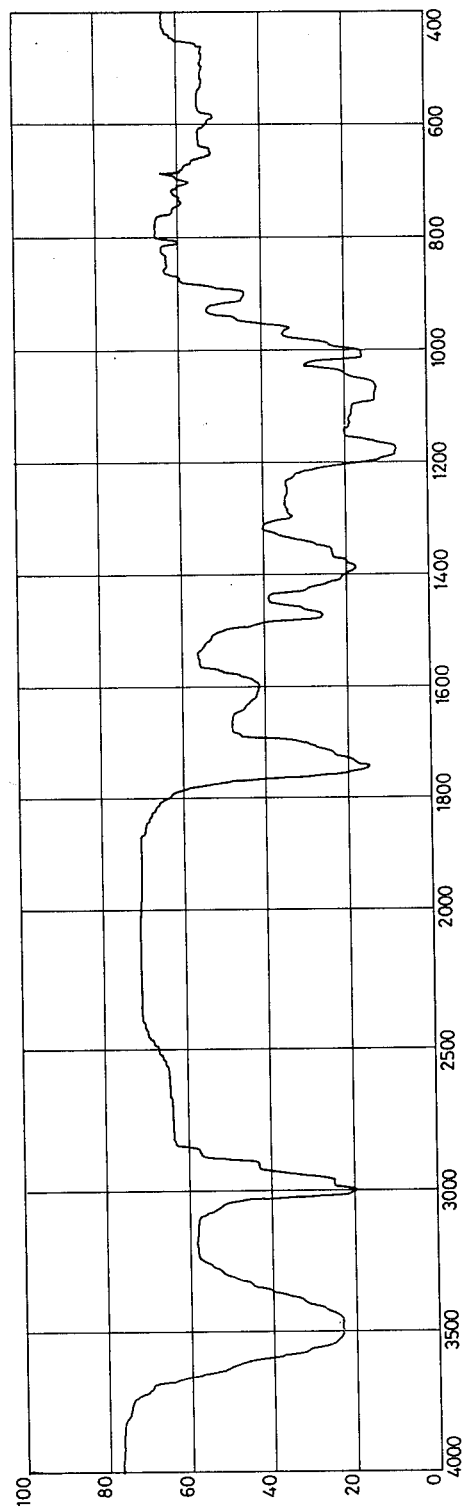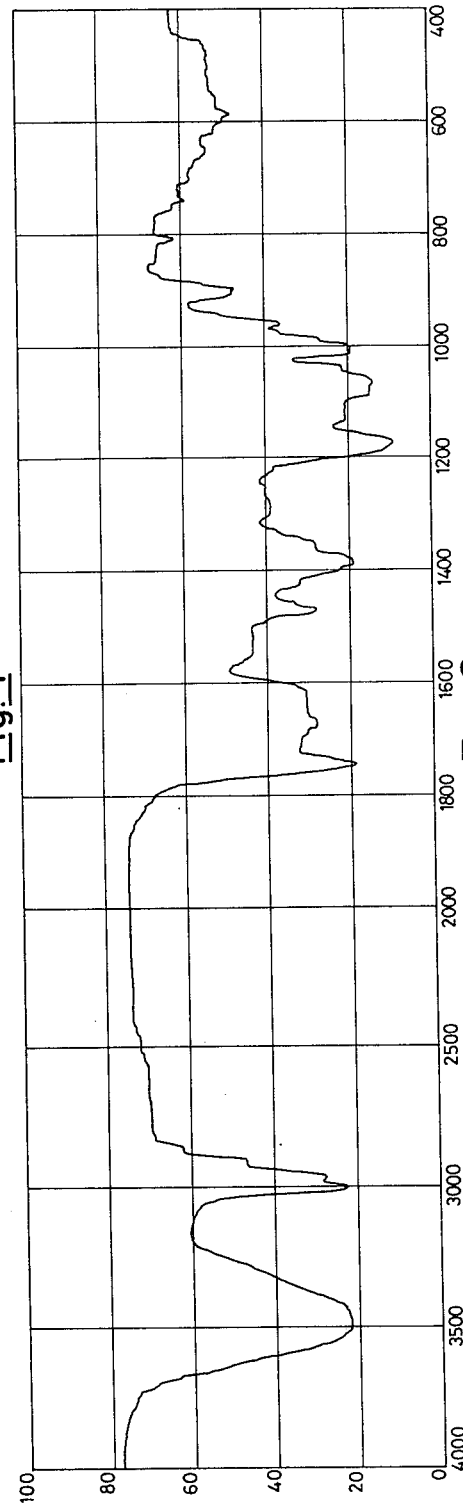
Fig. 1
Fig. 2

THIOLIC DERIVATIVES OF ERYTHROMYCIN HAVING THERAPEUTIC ACTIVITY, AND PHARMACEUTICAL COMPOSITIONS CONTAINING THEM

The present invention relates to novel thiolic derivatives of erythromycin and of the propionic ester of erythromycin, mainly salts of erythromycin with acids containing sulfur atoms in their molecule, in form of thioalcohol, thioether or thioester.

The exploitation of the therapeutical properties of thiolic compounds in combination with the properties of antibiotics has been already attempted.

However (C.A. 93 38279f) it was found that acetylcysteine and the derivatives thereof have an inhibiting action with respect to the activity of antibiotics. It has been now surprisingly found that the compounds of the present invention find therapeutical use in the cases in which erythromycin or the propionic ester thereof are already used and are generally characterized by a very low toxicity and by a high hematic concentration: these aspetcs are very important from the therapeutical point of view.

The derivatives according to the present invention have the following general formula $$R—X \qquad (1)$$

wherein R is a radical selected amongst the following radicals:

(1) acetylcysteine

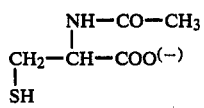

(2) carobxymethylcysteine

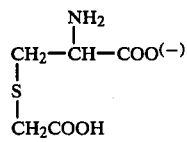

(3) thiazolidin-carboxylic acid

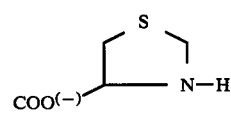

(4) mercapto-succinic acid

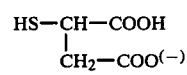

and X is the radical of erythromycin or of the propionyl ester of erythromycin having the formula

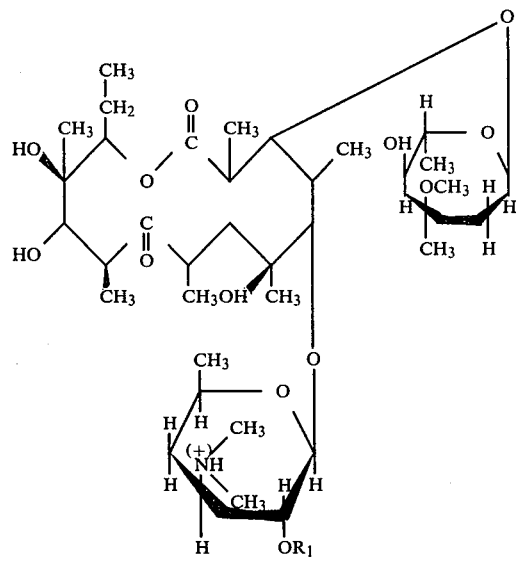

in which $R_1$ is H or $CH_3—CH_2—CO$.

The compounds according to the invention are white, microcrystalline powders.

Generally, the salt containing erythromycin monopropionyl ester is less soluble than the corresponding salt of erythromycin base; for both derivatives, moreover, the solubility increases in solvent mixtures, such as water-ethanol (1-5%), and water-ethylene glycol (1-5%).

Their use is foreseen under all pharmaceutical forms: capsules, solutions, injectable preparations, aerosols, creams, powders and suspensions, both for human beings and for veterinary use. Particularly for the salts of erythromycin base there are foreseen pharmaceutical preparations of the injectable type or administerable by aerosol, whereas for the derivatives of propionyl erythromycin there are preferred the orally administerable formulations and the suspensions. The compounds are affected by sun light, humidity and heat, and are true salts, both from the chemical and from the physical point of view.

The method for the preparation of the thiolic derivatives of erythromycin or of propionyl ester of erythromycin according to the present invention comprises reacting erythromycin base or the propionic ester of erythromycin with the acid, in a stoichiometrical ratio or in the presence of a slight excess of the antibiotic nucleous, and is characterized in that the reaction is carried out in an organic solvent, at a temperature of between 20° and 40° C. and in the presence of water in an amount not greater than 20%.

In fact, it has been found, in a surprising manner, that the presence of water preferably in an amount of 4-5% by volume with respect to the reaction solvent, permits the reaction to be completed with exceedingly good results. On the contrary, water amounts greater than 20% may cause the reaction product to be dissolved again in the aqueous/organic mixture.

The following examples, only given for illustrative purpose, disclose the preparation of the derivatives of the invention.

EXAMPLE 1

Erythromycin salt with mercapto-succinic acid 46.26 g (0.063 moles) of dry erythromycin base (namely a 2% excess with respect to the purely stoichiometrical reaction ratio) are dissolved in 350 mls of acetone at a temperature of between 15° and 40° C. This solution is added with 4.64 g of mercaptosuccinic acid, to obtain a clear and colorless solution.

Then 15 mls of water are added dropwise; a salt is very rapidly formed, which precipitates and tends to prevent the stirring. There are formed white microcrystals and the stirring is continued for about 1 hour.

The product is filtered under vacuum by means of a Buchner becker and acetonic mother liquors are obtained, being slightly yellow straw-coloured, which after evaporation give neglectable amounts of crystals.

The product is dried at a maximum temperature of 40° C. and 48.5 g of crystalline product are thus obtained (molecular weight 1618) with a yield of 97%.

The melting point is 133°–140° C. (with decomposition).

FIG. 1 shows the IR spectrum.

EXAMPLE 2

Salt of erythromycin with thiazolidin-4-carboxylic acid 42.32 g of erythromycin base are dissolved in 250 mls of methylisobutylketone until a clear solution is obtained; then, under stirring, the thiazolidin-4-carboxylic acid in finely divided form (7.6 g) is added and the stirring is continued until a total dispersion is obtained over about 30 minutes.

Then 9 mls of water are added dropwise, a vigorous stirring being maintained. A crystalline, white and fine precipitate is slowly formed over 2 hours. After standing for 1 hour the mixture is filtered under vacuum. After drying at the maximum temperature of 40° C., 45 g of solid produvct are obtained, with a yield of 90.2% of the theoretical value.

Figure 5:
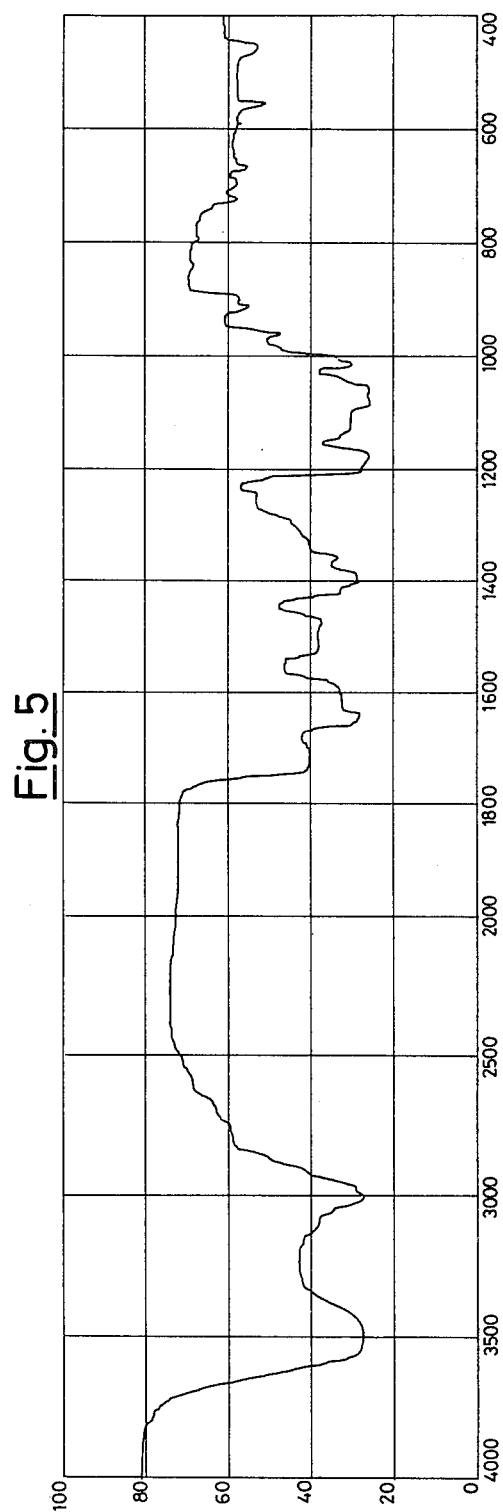

In the same manner the corresponding salt is prepared starting from 40.2 g of erythromycin and 9.8 g of carboxymethylcysteine, the product having melting point of 130°–140° C. and the IR spectrum shown in FIG. 5.

EXAMPLE 3

Salt of propionyl erythromycin with N-acetyl-L-cysteine 20 g of erythromycin propionate are dissolved in 30 mls of acetone and 70 mls of methylisobutylketone.

This solution is added with 4.1 g of N-acetyl-L-cysteine until a complete solution is obtained (under stirring).

The clear, slightly straw-coloured solution, is added, under stirring, with 2.5 mls of water. A precipitate of the salt is slowly formed, within about 2 hours.

After filtration under reduced pressure, 21.5 g of product are obtained with a yield of 80–83% of the theoretical value.

The IR spectrum is shown in FIG. 2.

The corresponding salt is likewise prepared starting from 20 g of erythromycin base and 4.45 g of N-acetyl-L-cysteine, and 20 g of the salt are obtained (with a yield of 82% of the theoretical value), the melting point being 128°–140° C.

The IR spectrum is shown in FIG. 3.

EXAMPLE 4

Salt of propionylerythromycin with sodium alpha-mercapto-hemisuccinate 3.8 g of alpha-mercaptosuccinic acid are dissolved in 10 mls of water with 2.12 g of sodium bicarbonate until the effervescence is terminated.

20 g of erythromycin propionate are dissolved at 30° C. in 20 mls of acetone and 100 mls of methylisobutylketone.

Under stirring, the solution of erythromycin propionate is added with the solution of sodium alpha-mercaptohemisuccinate and the mixture is heated to a maximum temperature of 40° C., the stirring being continued.

The salt is slowly formed and precipitates upon cooling.

The mixture is cold filtered under reduced pressure and washed with little methylisobutylketone.

The yield is 18.5 g (76.5% of the theoretical yield).

Figure 4:
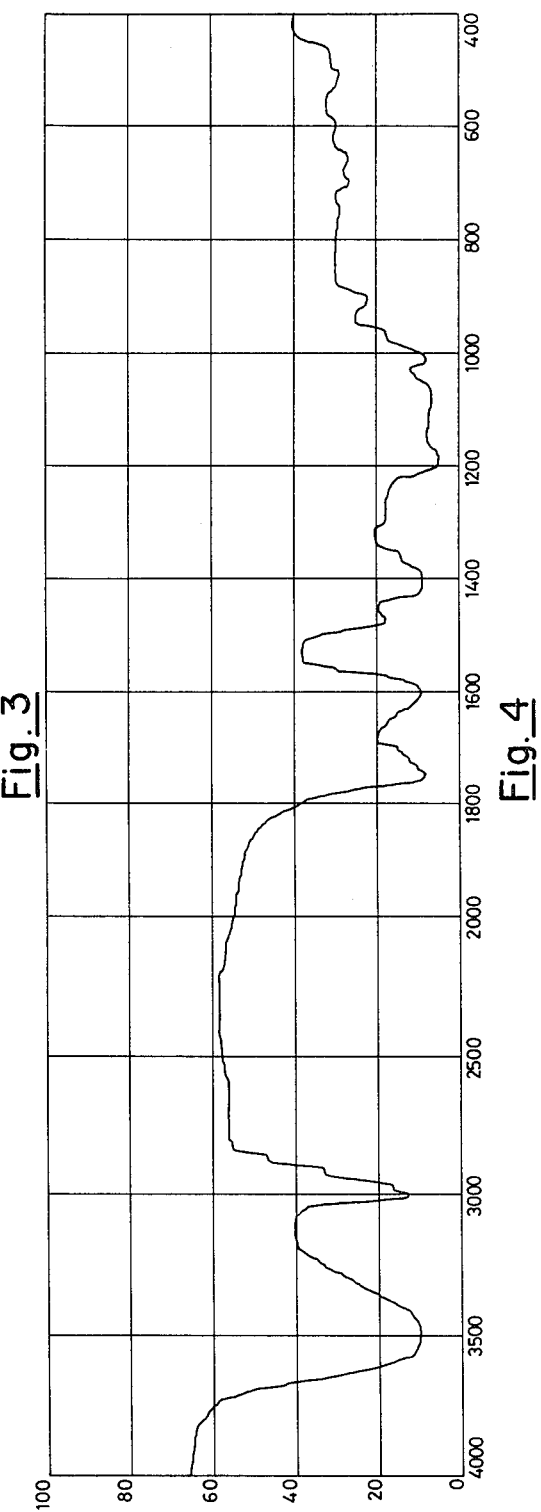

FIG. 4 shows the IR spectrum.

EXAMPLE 5

Salt of erythromycin propionate with mercapto-succinic acid 100 g of erythromycin propionate are dispersed in 400 mls of acetone, at room temperature and under stirring. Then 19 g of mercapto-succinic acid are added, by maintaining the mixture under stirring until a totally clear solution is obtained.

Then 20 mls of water are slowly added.

The salt precipitates with a yield of 96%, about 1 hour after the water addition.

The melting point is 122°–127° C.

The other salts of erythromycin propionate are likewise prepared.

The compounds of the invention have been subjected to toxicological, pharmacological and pharmacodynamic tests aiming to assess the toxicity (and consequently the possibility of use in the therapeutical field) and the therapeutical properties. In the hereinafter stated results the compounds of the invention are indicated by the following abbreviations:

RV/01—erythromycin alpha-mercaptosuccinate;
RV/03—erythromycyn-thiazolidin-carboxylate;
RV/04—erythromycin-S-carboxymethylcysteinate;
RV/05—erythromycin-N-acetylcysteinate;
RV/11—erythromycin-monopropionate-alpha-mercaptosuccinate;
RV/13—erythromycin-monopropionate-thiazolidincarboxylate;
RV/14—erythromycin-monopropionate-S-carboxymethyl cysteinate;
RV/15—erythromycin monopropionate N-acetylcysteinate

(A) Acute toxicity

The acute toxicity was assessed in Swiss white mice by oral and intravenous route. The $LD_{50}$ values have been calculated by the methods of Probits, starting from the mortality recorded 10 days after the treatment.

| Compound | Administration route | $LD_{50}$ mg.kg (reliability limits) |
|---|---|---|
| erythromycin | os | >3000 |
| erythromycin hy- | i.v. | 376.58 (478.78–296.20) |

| Compound | Administration route | LD$_{50}$ mg.kg (reliability limits) |
|---|---|---|
| drochloride | | |
| RV01 | os | >3000 |
| RV01 | i.v. | 458.49 (518.06–405.77) |
| RV03 | os | >3000 |
| RV03 | i.v. | 491.96 (552.31–438.20) |
| RV04 | os | >3000 |
| RV04 | i.v. | 439.46 (545.44–354.08) |
| RV05 | os | >3000 |
| RV05 | i.v. | 472.84 (529.08–442.57) |
| RV11 | os | 3000 |
| RV13 | os | 3000 |
| RV14 | os | 3000 |
| RV15 | os | 3000 |

(B) Antibacterial activity in vitro

The antibacterial activity in vitro of the compounds of the invention was assessed by comparing the different minimum inhibiting concentrations (MIC) with those of erythromycin base and of erythromycin estolate in Gram-positive and Gram-negative strains cultivated on Brain Heart Infusion (Difco). The tested samples of erythromycin estolate, RV11, RV13, RV14 and RV15 were previously hydrolized according to the prescription given in U.S. Pharmacopoeia, XX edition, page 1347.

In the following table I the MIC/ml values are indicated corresponding to the lowest concentration capable of inducing a complete inhibition of the bacterial development.

| | STRAIN | | ERYTHROMYCIN | ERYTHROMYCIN ESTOLATE | RV 01 | RV 03 | RV 04 | RV 05 | RV 11 | RV 13 | RV 14 | RV 15 |
|---|---|---|---|---|---|---|---|---|---|---|---|---|
| (1) | Staph. albus | SS 03 | 0.05 | 0.05 | 0.1 | 0.05 | 0.1 | 0.05 | 0.05 | 0.05 | 0.1 | 0.25 |
| (2) | | SS 04 | 0.05 | 0.05 | 0.05 | 0.025 | 0.05 | 0.025 | 0.05 | 0.025 | 0.05 | 0.05 |
| (3) | Staph. aureus | SS 07 | 0.025 | 0.205 | 0.05 | 0.025 | 0.025 | 0.025 | 0.05 | 0.025 | 0.025 | 0.025 |
| (4) | | SS 08 | 0.025 | 0.025 | 0.025 | 0.025 | 0.05 | 0.025 | 0.025 | 0.05 | 0.05 | 0.025 |
| (5) | | SS 09 | 0.1 | 0.05 | 0.1 | 0.05 | 0.025 | 0.1 | 0.1 | 0.1 | 0.1 | 0.05 |
| (6) | | SS 10 | 0.1 | 0.2 | 0.05 | 0.1 | 0.2 | 0.025 | 0.025 | 0.1 | 0.2 | 0.05 |
| (7) | Strept. haemolyticus | SS 17 | 3 | 3 | 3 | 1.5 | 1.5 | 3 | 1.5 | 1.5 | 1.5 | 1.5 |
| (8) | | SS 18 | 1.5 | 3 | 1.5 | 1.5 | 1.5 | 0.8 | 1.5 | 1.5 | 0.8 | 3 |
| (9) | Strept. faecalis | SS 19 | 0.1 | 0.1 | 0.1 | 0.05 | 0.05 | 0.2 | 0.05 | 0.05 | 0.05 | 0.05 |
| (10) | S. lutea | ATCC 9341 | 0.01 | 0.01 | 0.01 | 0.025 | 0.01 | 0.01 | 0.01 | 0.025 | 0.01 | 0.01 |
| (11) | B. subtilis | ATCC 6633 | 0.025 | 0.01 | 0.01 | 0.05 | 0.025 | 0.01 | 0.025 | 0.025 | 0.025 | 0.01 |
| (12) | | SS 127 | 0.05 | 0.025 | 0.01 | 0.025 | 0.025 | 0.01 | 0.05 | 0.025 | 0.05 | 0.025 |
| (13) | B. cereus | ATCC 11778 | 0.4 | 0.8 | 0.4 | 0.08 | 0.2 | 0.4 | 0.8 | 0.8 | 0.4 | 0.4 |
| (14) | B. anthranis | SS 08 | 0.4 | 0.4 | 0.4 | 0.2 | 0.4 | 0.4 | 0.8 | 0.4 | 0.4 | 0.4 |
| (14 bis) | | SS 09 | 0.4 | 0.4 | 0.4 | 0.4 | 0.2 | 0.4 | 0.4 | 0.4 | 0.8 | 0.4 |
| (15) | Br. melitensis | SS 19 | 3 | 3 | 3 | 6 | 6 | 3 | 3 | 3 | 3 | 3 |
| (16) | Br. abortus | SS 7 | 12 | 6 | 6 | 6 | 6 | 12 | 6 | 6 | 12 | 6 |
| (17) | Citrobacter | SS 05 | >200 | >200 | >200 | >200 | >200 | >200 | >200 | >200 | >200 | >200 |
| (18) | | SS 09 | >200 | >200 | >200 | >200 | >200 | >200 | >200 | >200 | >200 | >200 |
| (19) | S. infantis | SS 08 | 100 | 100 | 100 | 200 | 100 | 100 | 100 | 100 | 100 | 100 |
| (20) | S. heidelberg | SS 18 | 100 | 100 | 100 | 100 | 100 | 100 | 100 | 100 | 100 | 100 |
| (21) | E. cloacae | SS 07 | >200 | >200 | >200 | >200 | >200 | >200 | >200 | >200 | >200 | >200 |
| (22) | E. aerogenes | SS 011 | 100 | 50 | 50 | 50 | 50 | 100 | 100 | 50 | 50 | 50 |
| (23) | Ps. aeruginosa | SS 10 | 100 | 100 | 200 | 100 | 100 | 200 | 100 | 100 | 100 | 100 |
| (24) | | SS 12 | >200 | 200 | 200 | 200 | 200 | 200 | 200 | 100 | 100 | 200 |
| (25) | E. coli | SS 04 | 100 | 100 | 50 | 100 | 100 | 100 | 50 | 100 | 100 | 50 |
| (26) | | SS 05 | 50 | 100 | 50 | 50 | 50 | 25 | 100 | 50 | 50 | 100 |
| (27) | | SS 06 | 100 | 50 | 100 | 50 | 100 | 100 | 50 | 50 | 25 | 25 |
| (28) | | SS 07 | 50 | 50 | 25 | 50 | 25 | 25 | 50 | 50 | 50 | 50 |
| (29) | Pr. mirabilis | SS 09 | >200 | >200 | >200 | >200 | 200 | >200 | >200 | >200 | >200 | >200 |
| (30) | Pr. vulgaris | SS 10 | >200 | >200 | >200 | >200 | >200 | >200 | >200 | >200 | >200 | >200 |
| (31) | Kl. aerogenes | SS 71 | 50 | 100 | 100 | 50 | 50 | 50 | 100 | 100 | 100 | 100 |
| (32) | Kl. pneumoniae | SS 04 | 100 | 100 | 100 | 100 | 100 | 50 | 200 | 100 | 100 | 100 |
| (33) | Sr. marcescens | SS 03 | 200 | >200 | 200 | 100 | >200 | 200 | 200 | 100 | 200 | 200 |
| (34) | C. diphtheriae | SS 19 | 0.01 | 0.025 | 0.025 | 0.025 | 0.205 | 0.05 | 0.01 | 0.01 | 0.01 | 0.02 |
| (35) | D. pneumoniae | SS 23 | 0.05 | 0.05 | 0.05 | 0.025 | 0.05 | 0.05 | 0.025 | 0.025 | 0.05 | 0.05 |
| (36) | N. gonorreae | SS 27 | 0.8 | 0.8 | 0.8 | 0.8 | 0.8 | 0.8 | 0.4 | 0.8 | 0.8 | 0.8 |
| (37) | N. meningitidis | SS 04 | 0.8 | 1.5 | 0.8 | 1.5 | 1.5 | 0.8 | 1.5 | 0.8 | 0.8 | 0.8 |
| (38) | H. influentiae | SS 02 | 1.5 | 1.5 | 1.5 | 1.5 | 1.5 | 0.8 | 0.8 | 1.5 | 1.5 | 1.5 |
| (39) | H. pertussis | SS 03 | 0.4 | 0.4 | 0.4 | 0.4 | 0.8 | 0.2 | 0.4 | 0.2 | 0.4 | 0.2 |
| (40) | H. tubercolosis | SS 03 | 50 | 50 | 50 | 25 | 50 | 50 | 50 | 50 | 50 | 50 |
| (41) | C. albicans | SS 04 | 100 | 200 | >200 | 200 | 100 | 100 | 200 | 100 | 200 | 200 |
| (42) | Cl. tetani | SS 17 | 0.4 | 0.2 | 0.2 | 0.4 | 0.2 | 0.2 | 0.2 | 0.2 | 0.2 | 0.2 |

(C) Antibacterial activity in vivo

Experimental infection induced by *Staph. aureus* and *D. pneumoniae*

Swiss white mice of 20 g body weight were used, infected by parenteral administration of lethal amounts of pathogenic genes of *Staph. aureus* SS 07 and *D. pneumoniae* SS 23.

The protecting activity expressed as ED$_{50}$ mg/kg was assessed for erythromycin base, erythromycin estolate, RV01, RV03, RV04, RV05, RV11, RV13, RV14, and RV15 administered by oral route as well as for erythromycin ethyl succinate, RV01, RV03, RV04 and RV05 administered by subcutaneous route.

The antibiotics were administered at the time of injecting the infecting germ and 6 and 24 hours later. On the basis of the survival after 7 days, the ED$_{50}$ values were determined, as reported in the following table II and III, wherein the reliability limits are indicated in brackets.

TABLE II

Experimental infection by *Staph. aureus* SS 07
(ED$_{50}$ mg/kg of erythromycin)

| Compound | Administration route | ED$_{50}$ mg/kg (reliability limits) |
|---|---|---|
| erythromycin ethyl succinate | s.c. | 1.03 (1.34–0.79) |
| RV01 | s.c. | 0.95 (1.28–0.71) |
| RV03 | s.c. | 1.00 (1.36–0.73) |
| RV04 | s.c. | 1.00 (1.24–0.80) |
| RV05 | s.c. | 1.33 (1.61–1.10) |
| erythromycin | os | 2.09 (2.36–1.86) |
| erythromycin estolate | os | 2.20 (2.44–1.99) |
| RV01 | os | 2.36 (2.68–2.08) |
| RV03 | os | 2.14 (2.42–1.89) |
| RV04 | os | 2.31 (2.55–2.09) |
| RV05 | os | 2.08 (2.38–1.83) |
| RV06 | os | 2.02 (2.32–1.75) |
| RV11 | os | 2.14 (2.40–1.91) |
| RV13 | os | 2.20 (2.44–1.99) |
| RV14 | os | 2.26 (2.49–2.05) |
| RV15 | os | 2.10 (2.49–1.92) |

TABLE III

Experimental infection by *D. pneumoniae* SS 23
(ED$_{50}$ mg/kg of erythromycin)

| Compound | Administration route | ED$_{50}$ mg/kg (reliability limits) |
|---|---|---|
| erythromycin ethyl succinate | s.c. | 54.23 (69.76–42.16) |
| RV01 | s.c. | 52.70 (64.91–42.79) |
| RV03 | s.c. | 47.98 (59.13–38.93) |
| RV04 | s.c. | 60.17 (70.74–51.18) |
| RV05 | s.c. | 50.22 (62.33–40.46) |
| erythromycin | os | 113.53 (147.33–87.48) |
| erythromycin estolate | os | 127.89 (156.42–104.57) |
| RV01 | os | 108.98 (137.60–86.32) |
| RV03 | os | 119.21 (142.60–99.65) |
| RV04 | os | 119.31 (152.88–92.95) |
| RV05 | os | 119.31 (150.05–94.87) |
| RV11 | os | 100.41 (122.52–82.30) |
| RV13 | os | 113.88 (144.73–89.60) |
| RV14 | os | 123.74 (148.77–102.92) |
| RV15 | os | 110.90 (135.28–90.92) |

(D) Pharmacodynamics (a) In the rat.

The absorption by oral route of the differents salts of erythromycin was investigated in Sprague-Dawley male rats which were administered, in groups of 6 animals fasted since 12 hours, with erythromycin, erythromycin estolate, RV01, RV03, RV04, RV05, RV11, RV13, RV14, RV15 at the dose of 100 mg/kg (expressed as erythromycin) by oral route (gastric probing).

The blood samples were taken 0.30, 1, 2, 3, 4, 5 and 6 hours after the administration. For the dosing the microbiological method, and as the test micro-organism, *B. subtilis* were used. The experimental results are reported in the following table IV:

TABLE IV

| | | Hematic levels in the rat (average plus standard error) | | | | | | |
|---|---|---|---|---|---|---|---|---|
| Compound | N. of animals | mcg/ml after ... hours | | | | | | |
| | | 0.30 | 1 | 2 | 3 | 4 | 5 | 6 |
| erythromycin | 6 | 0.71 | 1.03 | 1.15 | 1.05 | 0.37 | 0.26 | 0.03 |
| | | 0.19 | 0.23 | 0.24 | 0.22 | 0.10 | 0.08 | — |
| erythromycin estolate | 6 | 0.68 | 1.74 | 2.49 | 1.49 | 0.61 | 0.37 | 0.04 |
| | | 0.07 | 0.14 | 0.35 | 0.22 | 0.10 | 0.05 | 0.01 |
| RV01 | 6 | 0.48 | 0.79 | 1.18 | 0.77 | 0.44 | 0.24 | 0.03 |
| | | 0.11 | 0.15 | 0.24 | 0.17 | 0.12 | 0.08 | 0.05 |
| RV03 | 6 | 0.58 | 0.71 | 1.30 | 0.77 | 0.59 | 0.36 | 0.07 |
| | | 0.14 | 0.14 | 0.34 | 0.17 | 0.14 | 0.10 | 0.02 |
| RV04 | 6 | 0.50 | 0.71 | 1.30 | 1.04 | 0.68 | 0.43 | 0.15 |
| | | 0.14 | 0.17 | 0.29 | 0.28 | 0.21 | 0.15 | 0.08 |
| RV05 | 6 | 0.44 | 0.83 | 1.41 | 1.03 | 0.59 | 0.40 | 0.08 |
| | | 0.07 | 0.22 | 0.38 | 0.28 | 0.16 | 0.12 | 0.01 |
| RV11 | 6 | 0.72 | 1.64 | 2.50 | 1.31 | 0.58 | 0.38 | 0.08 |
| | | 0.16 | 0.19 | 0.27 | 0.21 | 0.22 | 0.14 | 0.02 |
| RV13 | 6 | 0.81 | 1.80 | 2.47 | 1.10 | 0.72 | 0.52 | 0.12 |
| | | 0.07 | 0.10 | 0.23 | 0.17 | 0.11 | 0.11 | 0.05 |
| RV14 | 6 | 0.72 | 1.85 | 2.55 | 1.39 | 0.65 | 0.54 | 0.07 |
| | | 0.10 | 0.09 | 0.12 | 0.08 | 0.10 | 0.10 | 0.01 |
| RV15 | 6 | 0.85 | 1.90 | 2.68 | 1.19 | 0.55 | 0.44 | 0.03 |
| | | 0.23 | 0.08 | 0.15 | 0.08 | 0.03 | 0.04 | — |

(B) In the healthy volunteer

Group of 5 healthy volunteers, fasted since 24 hours, were administered by oral route with erythromycin estolate, RV11, RV13, RV14, RV15, at a dose of 500 mg of erythromycin.

The blood samples were taken 0.30, 1, 2, 3 and 4 hours after the administration.

For the dosing, the microbiological method using a *B. subtilis* strain was adopted.

The results are indicated in table V.

TABLE V

| | | Hematic levels in the healthy volunteer (average plus standard error) | | | | | | |
|---|---|---|---|---|---|---|---|---|
| Compound | No. of animals | mcg/ml after ... hours | | | | | | |
| | | 0.30 | 1 | 2 | 3 | 4 | 5 | 6 |
| erythromycin estolate | 5 | 0.27 | 0.58 | 2.10 | 1.41 | 1.31 | — | — |
| | | 0.05 | 0.09 | 0.17 | 0.07 | 0.08 | — | — |
| RV11 | 5 | 1.28 | 1.70 | 2.16 | 1.48 | 1.21 | — | — |
| | 5 | 0.12 | 0.09 | 0.12 | 0.08 | 0.05 | — | — |
| RV13 | 5 | 1.16 | 1.67 | 2.21 | 1.67 | 1.29 | — | — |
| | | 0.03 | 0.07 | 0.11 | 0.09 | 0.10 | — | — |
| RV14 | 5 | 1.20 | 1.78 | 2.28 | 1.60 | 1.21 | — | — |
| | | 0.07 | 0.04 | 0.06 | 0.14 | 0.06 | | |
| RV15 | 5 | 1.10 | 1.58 | 2.17 | 1.72 | 1.38 | | |
| | | 0.09 | 0.05 | 0.14 | 0.09 | 0.06 | | |

(E) Mucolytic activity

There was used the method described by Quevauviler et al (Thérapie 22, 485,1967) according to which a bronchial hypersecretion is induced after exposure of the animal to an aerosol treatment with SO$_2$. The test was carried out on Sprague Dawley male rats.

All rats were daily subjected to SO$_2$ inhalations, at a 0.03% concentration. After 50 hours of inhalation, the animals were divided in groups comprising 10 animals each. One group was not treated (control animals), whereas the other animals were treated, two hours per day, for 15 days consecutively with inhalations of SO$_2$ and with erythromycin estolate and RV11, RV13, RV14, RV15, by oral route at the dose of 500 mg/kg as well as with erythromycin ethyl succinate and RV01, RV03, RV04, RV05, by intramuscular route at the dose of 250 mg/kg.

The day after the last treatment, the anesthetized animals were sacrificed, and the lungs were removed and prepared for the microscopical and macroscopical examination. The results are indicated in the following Table VI.

TABLE VI

Qualitative and quantitative evaluation of the obstruction of the bronchial tract (% incidence)

| Treatment | administration route | Total obstruction | | | Partial obstruction |
|---|---|---|---|---|---|
| | | compact plug | nodular mass | pimply mass | |
| SO₂ (control) | — | 40 | 13.33 | 6.66 | 26.66 |
| SO₂ + erythromycin estolate 500 mg/kg | oral | 46.66 | 20 | 6.66 | 20 |
| SO₂ + RV11 500 mg/kg | oral | 20 | 6.66 | 6.66 | 13.33 |
| SO₂ + RV13 500 mg/kg | oral | 20 | 6.66 | 13.33 | 20 |
| SO₂ + RV14 500 mg/kg | oral | 26.66 | 6.66 | 6.66 | 13.33 |
| SO₂ + RV15 500 mg/kg | oral | 20 | 13.33 | 6.66 | 6.66 |
| SO₂ + erythromycin ethyl succinate 250 mg/kg | i.m. | 53.33 | 26.66 | 13.33 | 20 |
| SO₂ + RV01 250 mg/kg | i.m. | 26.66 | 6.66 | 13.33 | 13.33 |
| SO₂ + RV03 250 mg/kg | i.m. | 26.66 | 20 | 6.66 | 6.66 |
| SO₂ + RV04 250 mg/kg | i.m. | 20 | 13.33 | 6.66 | 13.33 |
| SO₂ + RV05 250 mg/kg | i.m. | 20 | 13.33 | 6.66 | 6.66 |

Thereafter the histological examination of both control and treated animals was carried out.

(1) Control animals subjected to a SO₂ inhalation

The macroscopical bronchial obstructions as detected by the hystological examination correspond to a mucus mass admixed with fibrin and infiltrated with polynuclear elements. The hypersecretion does equally concern the peripheral bronchioles and the alveoles.

As regards the bronchial epithelium there is revealed a proliferation of cup-shaped cells. The hyperplasy of the main bronchus appears as a stratification of 7 to 8 layers, associated to a bronchial hypertrophy.

(2) Animals treated with erythromycin estolate at the dose of 500 mg/kg by oral route and with erythromycin ethyl succinate at the dose of 250 mg/kg by intramuscular route From the histological examination it appears that the bronchial obstruction is formed by abundant mucus admixed with fibrin.

Due to the irritating effect of SO₂, the bronchial epithelium reacts through a proliferation of cells, mainly cup-shaped cells. The hyperplasy is associated in a number of cases to a bronchial hypertrophy. In some cases, mucus secreting cells appear in the peripheral bronchioles.

(3) Animals treated with RV11, RV13, RV14, RV15, at the dose of 500 mg/kg by oral route In the animals having, under macroscopical examination, a free non obstructed bronchial tract, the histological examination revealed the presence of bronchi having almost normal appearance. An epithelial hyperplasy with a number of cup-shaped cells and reduced intra-bronchial muco-purulents masses was detected.

The hystological appearance of the obstructed bronchial tracts is fully like that of the control animals.

(4) Animals treated with RV01, RV03, RV04, RV05, at the dose of 250 mg/kg by intramuscular route The histological examination as carried out in the animals which under macroscopical examination had free non obstructed bronchi, revealed a practically normal appearance. In some animals, the presence of an epithelial hyperplasy was detected with cup-shaped cells associated to intra-bronchial muco-purulent masses. The histological examination of the animals showing an obstructed bronchial tract, revealed an appearance like that of the control animals.

Conclusions

From the toxicity tests it results that the erythromycin salts are devoid of toxicity when administered by oral route. When injected, they can be slightly toxic and have however LD₅₀ values comparable with that of erythromycin.

From the tests of antibacterial activity in vitro it results that the erythromycin salts are active in a proportion like that of the erythromycin base.

From the tests of antibacterial activity in vivo and from the pharmacodynamic tests it results that the compounds RV01, RV03, RV04, RV05 are poorly absorbed by oral route and in a rate like that of erythromycin base.

The propionic derivatives RV11, RV13, RV14, RV15 are absorbed by oral route in a rate practically analogous to that of erythromycin estolate. Contrarywise to erythromycin estolate, the drugs according to the invention are endowed with a good mucolytic activity which is revealed in the animals treated by SO₂ inhalation.

I claim:

1. Thiolic derivatives of erythromycin and of 2'-propionic ester of erythromycin having the formula:

R—X  (1)

wherein R represents a radical selected from the group consisting of (1) carboxymethylcysteine

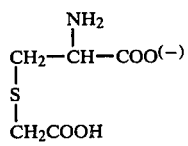

$$\begin{array}{c} NH_2 \\ | \\ CH_2-CH-COO^{(-)} \\ | \\ S \\ | \\ CH_2COOH \end{array}$$

(2) thiazolidin-4-carboxylic acid

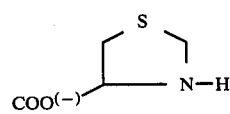

(3) mercapto-succinic acid

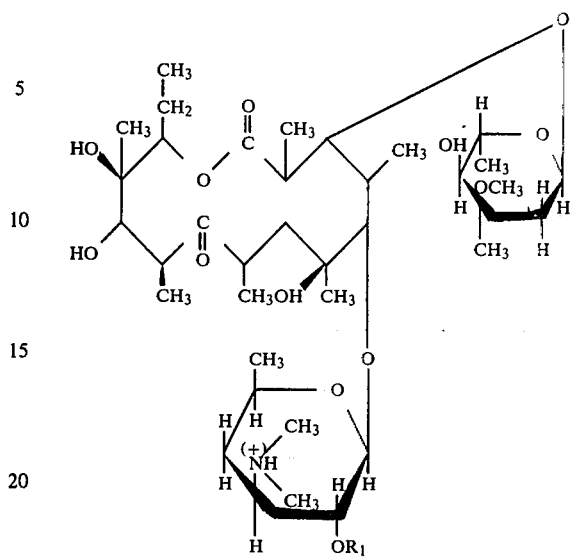

and X is the radical of erythromycin or of the propionic ester of erythromycin having the formula:

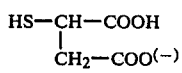

in which $R_1$ is H or $CH_3—CH_2—CO$.

2. The erythromycin salt of mercaptosuccinic acid according to claim 1.

3. The erythromycin salt of thiazolidin-4-carboxylic acid according to claim 1.

4. The erythromycin salt of carboxymethylcysteine according to claim 1.

5. The erythromycin 2'-propionic ester salt of acetylcysteine.

6. The erythromycin 2'-propionic ester salt of mercapto-succinic acid according to claim 1.

7. The erythromycin 2'-propionic ester salt of thiazolidin-4-carboxylic acid according to claim 1.

8. The erythromycin 2'-propionic ester salt of carboxymethylcysteine according to claim 1.

9. A process of administering to an animal in need of an antibiotic a compound according to claim 1 in an amount effective as an antibiotic.

10. A process according to claim 9 wherein the compound is administered orally.

11. A process of administering to an animal in need of mucolytic agent a compound according to claim 1 in an amount effective as a mucolytic.

12. A process according to claim 11 wherein the compound is administered orally.

* * * * *